United States Patent [19]

Brennan et al.

[11] Patent Number: 4,605,678

[45] Date of Patent: Aug. 12, 1986

[54] SEPARATION OF CATALYST FROM SLURRY BUBBLE COLUMN WAX AND CATALYST RECYCLE

[75] Inventors: James A. Brennan; Arthur W. Chester; Yung-Feng Chu, all of Cherry Hill, N.J.

[73] Assignee: Mobil Oil Corporation, New York, N.Y.

[21] Appl. No.: 720,916

[22] Filed: Apr. 8, 1985

Related U.S. Application Data

[63] Continuation-in-part of Ser. No. 479,523, Mar. 28, 1983, abandoned.

[30] Foreign Application Priority Data

Mar. 12, 1984 [ZA] South Africa ............... 84/1832

[51] Int. Cl.$^4$ .............................................. C07C 1/04
[52] U.S. Cl. .................................... 518/700; 518/702; 518/717; 518/722; 518/728; 44/54; 585/310; 585/407; 48/197 R; 208/950
[58] Field of Search ............... 518/700, 722, 702; 44/54; 585/310, 407; 48/197 R; 208/950

[56] References Cited

U.S. PATENT DOCUMENTS

| | | |
|---|---|---|
| 2,438,029 | 3/1948 | Atwell . |
| 2,651,655 | 9/1953 | Loughran . |
| 2,671,103 | 3/1954 | Kolbel et al. . |
| 2,775,607 | 12/1956 | Kolbel et al. . |
| 4,252,736 | 2/1981 | Haag et al. . |
| 4,423,265 | 12/1983 | Chu et al. . |

OTHER PUBLICATIONS

Farley et al., J. Institute of Petroleum, vol. 50, No. 482, Feb. 1964, pp. 27–46.
Hirschbein et al., Chem. Tech., Mar. 1982, pp. 172–179.

*Primary Examiner*—Howard T. Mars
*Attorney, Agent, or Firm*—Alexander J. McKillop; Michael G. Gilman; L. G. Wise

[57] ABSTRACT

A process for removing catalyst fines from the wax product produced in a slurry Fischer-Tropsch reactor comprises removing the wax product from the reactor and separating the catalyst fines by passing the wax product through a high gradient magnetic field, whereby the catalyst fines are held by a magnetized filter element and the wax product passes through unhindered to form a purified wax product which is ready for upgrading. The separated catalyst fines are returned to the reactor by backwashing the filter element.

33 Claims, 1 Drawing Figure

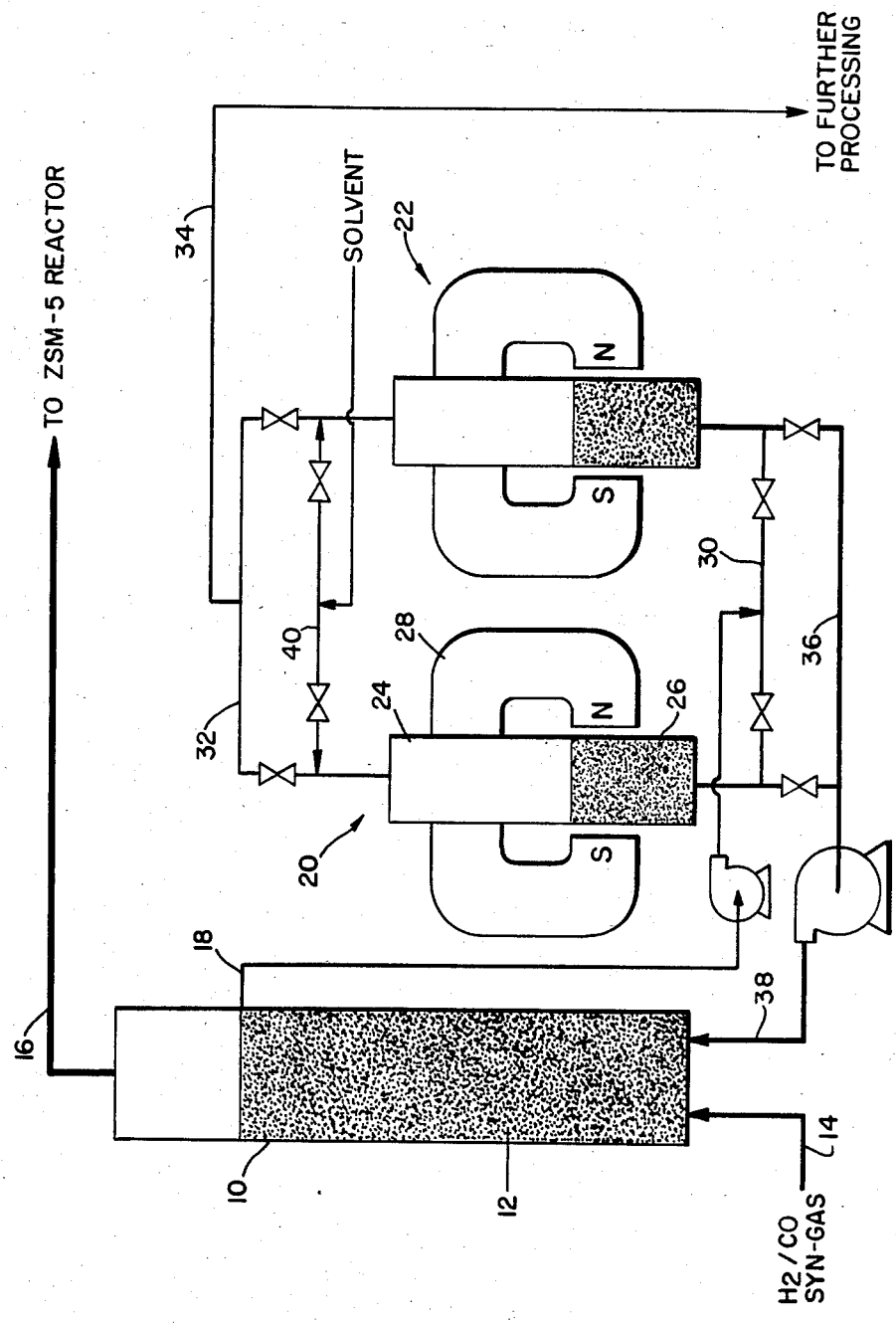

SEPARATION OF CATALYST FROM SLURRY BUBBLE COLUMN WAX AND CATALYST RECYCLE

CROSS-REFERENCE TO RELATED APPLICATIONS

This application is a continuation-in-part of U.S. Application Ser. No. 479,523, filed Mar. 28, 1983 now abandoned.

BACKGROUND OF THE INVENTION

1. Field of the Invention

This invention is concerned with a process for converting synthesis gas, i.e., mixtures of gaseous carbon oxides with hydrogen or hydrogen donors, to hydrocarbon mixtures and oxygenates. In one aspect, this invention is concerned with a process to convert such synthesis gas to hydrocarbon mixtures under conditions permitting good temperature control of the known exothermic reduction of carbon monoxide with hydrogen. In still another aspect, this invention concerns improvements in the process for effecting the hydrogenation of carbon monoxide in the presence of a liquid suspension of catalyst and, in particular, relates to the magnetic separation of catalyst fines and the removal of other undesirable compounds from the wax product which is produced before wax upgrading.

2. Description of the Prior Art

Processes for the conversion of coal and other hydrocarbons, such as natural gas to a gaseous mixture consisting essentially of hydrogen and carbon monoxide, or of hydrogen and carbon dioxide, or of hydrogen and carbon monoxide and carbon dioxide, are well known. An excellent summary of the art of gas manufacture, including synthesis gas, from solid and liquid fuels is given in *Encyclopedia of Chemical Technology*, edited by Kirk-Othmer, Second Edition, Vol. 10, pp. 353–433 (1966), Intersciences Publishers, New York, N.Y., the contents of which are herein incorporated by reference. The particular techniques for gasification of coal or other solid, liquid, or gaseous fuel are not considered to be a part of this invention, although such techniques may be an important consideration in overall process efficiency.

It is considered to be desirable to effectively and more efficiently convert synthesis gas, and thereby coal and natural gas, to highly valued hydrocarbons, such as motor gasoline with high octane number, petrochemical feedstocks, liquefiable petroleum fuel gas, and aromatic hydrocarbons. It is well known that synthesis gas will undergo conversion to form reduction products of carbon monoxide, such as hydrocarbons, at temperatures in the range of from about 350° F. to about 850° F. and under pressures in the range of from about 1 to 1000 atmospheres, over a fairly wide variety of catalysts. The Fischer-Tropsch process, for example, which has been most extensively studied, produces a wide range of products including waxy materials, oxygenates and liquid hydrocarbons, a portion of which have been successfully used as low octane gasoline. The types of catalysts that have been studied for this and related processes include those based on metals or oxides of iron, cobalt, nickel, ruthenium, thorium, rhodium and osmium with and without promoters.

The range of catalysts and catalyst modifications disclosed in the art encompasses an equally wide range of conversion conditions for the reduction of carbon monoxide by hydrogen and provides considerable flexibility toward obtaining selected boiling range products. A review of the status of this art is given in "Carbon Monoxide-Hydrogen Reactions", *Encyclopedia of Chemical Technology*, edited by Kirk-Othmer, Second Edition, Vol. 4, pp. 446–448, Interscience Publishers, New York, N.Y., the text of which is incorporated herein by reference. See also H. H. Storch, N. Golumbic and R. B. Anderson, "The Fischer-Tropsch and Related Synthesis", John Wiley & Sons, Inc., New York, N.Y.

The hydrogenation of carbon oxides to highly valued hydrocarbons by the Fischer-Tropsch process is highly exothermic and thus, the reaction system must include means to remove the heat of reaction. This is particularly important if a low $H_2/CO$ ratio synthesis gas is being converted. While low $H_2/CO$ ratio gas can be produced more cheaply than high $H_2/CO$ ratio gas, low $H_2/CO$ ratio gas cannot easily be converted to transportation fuels in conventional, fixed-bed reactors because of the difficulty in temperature control. The high temperatures of reaction and high carbon monoxide partial pressures favor carbon monoxide disproportionation and carbon formation which results in catalyst cementation. This can be shown by the following reaction:

$$2CO \rightarrow C + CO_2$$

For the purpose of furnishing better temperature control for Fischer-Tropsch type synthesis, in particular, if a low $H_2/CO$ ratio synthesis gas is converted, it has been proposed to suspend the finely divided catalyst in a liquid medium, and preferably a hydrocarbon mixture such as may be, for instance, obtained by way of the higher boiling components of the synthesis products. The suspension can then be subjected to cooling to continuously remove excess heat therefrom.

The slurried-catalyst reactor system otherwise identified as a suspended Fischer-Tropsch catalyst in a liquid medium suitable for the purpose of converting syngas to hydrocarbon products has been the subject of numerous patents. Early patents on the subject are U.S. Pat. Nos. 2,438,029; 2,671,103; 2,680,126; 2,775,607; 2,852,350; and numerous others.

In U.S. Pat. No. 4,252,736, a patent related to the objectives of the present invention as more defined herein below, the conversion of coal to gaseous and liquid products is achieved by the high efficiency gasification of coal to a low $H_2/CO$ ratio syngas, conversion of the low ratio syngas with a water gas shift slurry Fischer-Tropsch catalyst to a product comprising $C_1$ to $C_{80}$ hydrocarbons and oxygenates, and conversion of the Fischer-Tropsch product to premium gas and increased liquid products comprising gasoline, distillate and lubes over a special zeolite catalyst exemplified by ZSM-5. According to the patent, a coal, coke or coal char gasifier with a low steam to oxygen ratio as well as low steam to coal ratio, such as provided by the British Gas Corporation-Lurgi slagging gasifier, has significant advantages in terms of thermal efficiency and cost and can lead to a reduction of up to 20 to 40% in syngas production costs. This advantage is larger for Eastern bituminous coal which has a lower reactivity. See Table 1 below.

TABLE 1

Lurgi Dry Ash Versus BGC-Lurgi Slagger

| Coal | Lurgi Dry Ash Western | Lurgi Dry Ash Eastern | BGC-Lurgi Slagger Frances (Scottish Non-Caking Reactive) | BGC-Lurgi Slagger Eastern | BGC-Lurgi Slagger North Dakota Lignite |
|---|---|---|---|---|---|
| Gasifier Itself | | | | | |
| Scf $O_2$/mscf Syngas | 135 | 187 | 168 | 157 | 189 |
| lb Steam/mscf Syngas | 46 | 75 | 10.6 | 8.6 | 9.1 |
| Steam/Oxygen | 7.5 | 8.5 | 1.3 | 1.15 | 1.0 |
| $H_2$/CO Ratio | 2.1 | 2.8 | 0.50 | 0.52 | 0.5 |
| Cold Gas Efficiency, % (adjusted for tars) | 80 | 76 | 89 | 90 | 91.0 |
| $CH_4$/CO + $H_2$ | 0.78 | 0.6 | 0.32 | 0.35 | 0.32 |
| Net Efficiency, % Including Shift to Hydrogen-to-CO Ratio to 2 | 71 | 59 | 78 | 78 | 79 |
| lb Steam/mscf Syngas (Total) | 46 | 75 | 40 | 39 | 39 |
| Net Efficiency, % | 71 | 59 | 71 | 70 | 71 |

However, a penalty is paid for this gain. The product gas of the slagging gasifier has an $H_2$/CO ratio of about 0.5 to 0.8 as compared to a ratio of about 2.0 produced by more costly gasifiers. The most advanced known Fischer-Tropsch process, practiced commercially at SASOL in South Africa, requires a synthesis gas with an $H_2$/CO ratio exceeding 2:1, produced in a Lurgi Dry Ash gasifier. If synthesis gas were produced in a more economical gasifier in a low $H_2$/CO ratio, it would require a shift conversion to increase its $H_2$/CO ratio to the level about 2:1 as required. Such shift reaction consumes a considerable amount of energy, especially in the form of steam, largely negating the high thermal efficiency of this gasifier. This is illustrated by the date in Table 1, which lists the steam requirements for shifting a low ratio $H_2$/CO gas to a high ratio of 2:1 as well as the reduction in thermal efficiency for the gas production. When using a western type coal (e.g., Frances), shifting to a ratio of 2:1 wipes out the advantage in thermal efficiency. In this operation, a slightly lower steam consumption requirement is offset by the higher oxygen consumption required by the operation. However, when using an eastern coal, the slagging gasifier with a subsequent shift of low ratio $H_2$/CO gas to 2:1 is still very significantly better than a prior art gasifier by Lurgi.

An efficient gasifier is identified as one having the characteristics of:
(a) using a low steam to dry, ash-free coal weight ratio of less than 1.0 or a low ratio of steam to syngas produced of less than 30 lbs. steam per mscf syngas;
(b) producing a syngas with an $H_2$/CO ratio equal to or less than 1; and
(c) a low temperature of the gasifier exit gas of less than 2000° F.

Examples of gasifiers satisfying the above characteristics include slagging type gasifiers, such as the British Gas Corporation-Lurgi slagger or the Secord-Grate slagging gasifier or fluidized bed gasifiers, such as the U-Gas and Westinghouse gasifiers.

Any gasifier capable of producing a synthesis gas is applicable in the present invention. The significance of the above discussion lies in the efficiency which is gained by producing low $H_2$/CO ratio syngas. Such low ratio syngas when reacted in a Fischer-Tropsch system is highly exothermic and, as such, a slurry Fischer-Tropsch process is highly desirable to remove process heat as previously described.

Often, the catalyst employed for Fischer-Tropsch synthesis are complete free from activators and consist essentially of the metals of Group VIII of the Periodic Table as defined above, or their compounds only. It is thus desirable, and often required, to add suitable activating substances conventionally known and used for synthesis of the Fischer-Tropsch type. Copper, for example, is such an activating additive for iron catalyst. Cobalt or nickel may be activated by the addition of Th, Mg or Cu or their compounds. For a further increase in activity, alkali compounds are often added to the catalysts. For example, in U.S. Pat. No. 2,671,103, a slurry Fischer-Tropsch reaction system is operated to maintain a predetermined range of alkali content by adding to the catalyst material to be freshly introduced or adding together with such material a somewhat higher alkali content than is ordinarily contained in the catalyst material within the reactor at that time. Suitable alkali compounds are the oxides, hydro-oxides, carbonates, hydrocarbonates, phosphates, silicates and borates of sodium and potassium, furthermore their formates, acetates or the salts of higher organic acids, such as soaps.

The organic product formed in a slurry Fischer-Tropsch process contains olefins, paraffins and oxygenated hydrocarbons with carbon numbers from 1 to about 80. Only those compounds vaporized at the reactor conditions plus some entrained molecules will appear in the overhead effluent. The remainder, a high molecular weight wax, remains in the slurry oil. At conditions which yield only a few percent methane, 25% by weight or more of the product may be high molecular weight wax. At certain reaction conditions the viscosity of the wax increases during reaction, such that the slurry nears the point of gellation. A slurry medium is said to have gelled when it will not flow under gravity. If the slurry approaches gellation at reaction conditions, the reaction must be shut down.

During normal operation, the high molecular weight wax is periodically withdrawn to prevent build-up of such wax in the reactor and to prevent gellation of the slurry and reactor shutdown. When such draw-off of the wax is made, the wax contains entrained catalyst fines which need to be removed prior to upgrading the wax and which must be available for use in the process. In an article by R. Farley and D. J. Ray, *Journal of the Institute of Petroleum*, Vol. 50, No. 482, p. 31, February 1964, there is described the use of laboratory tests in order to find a method of wax withdrawal from a Fischer-Tropsch reactor which was capable of high withdrawal rates and which would still leave the catalyst available for use within the plant. Various magnetic, sintered-metal, and woven-wire cloth filters were shown to be unsuitable for the conditions of temperature, pressure or particle size utilized, and none of the filtering methods investigated gave adequate throughputs.

In "Magnetic Separation in Chemistry and Biochemistry", by Bernard L. Hirschbein et al, *Chemtech,* March 1982, pp. 172-178, the authors contend that use of magnetic separation can be increased in chemcial applications. Among suggested uses of magnetic separation is the removal of used catalyst-derived impurities from products such as Fischer-Tropsch catalysts. The article discloses that simple methods of generating very high magnetic field gradients have been developed. One such simple design comprises magnetic stainless steel wool pushed into a tube and the tube placed between the poles of magnet. Magnetic particles, such as in an aqueous suspension, would be retained by the steel wool and the water carrier would pass through unhindered. The high magnetic gradient is achieved by the intersection of the external magnetic field of the magnet and the local magnetic field produced by the magnetic filter element, e.g., steel wool, steel rods, filaments, etc.

An object of the present invention is to provide an improved process for catalytically hydrogenating carbon oxides in the presence of a finely divided catalyst in liquid suspension.

Another object of the invention is to provide an improved process for the removal of catalyst fines from the wax product which is recovered from a slurry Fischer-Tropsch reactor. A further object is to provide an improved process for the recovery and recycle of catalyst fines which are contained in the high molecular weight products removed from a slurry Fischer-Tropsch reactor. Still another object is to remove other undesirable compounds from the wax product which is removed from the slurry Fischer-Tropsch reactor so as to yield a pure wax product prior to wax upgrading. Other objects will become apparent from the following description of the invention.

SUMMARY OF THE INVENTION

In accordance with the present invention, the wax product recovered from a slurry Fischer-Tropsch reactor is purified to the extent that substantially all of the catalyst fines which are contained in the recovered wax product are separated from the wax product prior to wax upgrading. The catalyst particles which are contained in the recovered wax product and which are subsequently removed from the wax are recycled into the slurry Fischer-Tropsch reactor. Separation of the catalyst fines from the wax product is accomplished by high gradient magnetic separation in which the wax is melted and the melted wax passed through a high gradient magnetic field. The wax passes through the field while the catalyst fines which are typically iron are held by magnetized filter elements which form a portion of the magnetic field. The purified wax can be subsequently upgraded by various methods, such as hydrogenation, isomerization, hydrocracking, conversion to gasoline, distillate and/or lubes over ZSM-5 crystalline aluminosilicate zeolite, etc. To recycle the separated catalyst the magnetic field is removed and the filter elements are washed with a carrier fluid and the washings returned to the slurry bed reactor.

BRIEF DESCRIPTION OF THE DRAWING

The FIGURE is a schematic illustration of one possible process scheme for separating Fischer-Tropsch catalyst fines from the wax product of a slurry Fischer-Tropsch reactor.

DESCRIPTION OF SPECIFIC EMBODIMENTS

The synthesis gas usable in accordance with the invention is the conventional gas mixture generally applicable to the synthesis of hydrocarbon products in accordance with a carbon monoxide hydrogenation procedure of the Fischer-Tropsch type. Such synthesis gas may include a gas product, such as formed by the gasification of coal, or may have been generated in any other suitable manner well known in the art for this type of reaction. The charge for the slurry Fischer-Tropsch reactor may contain an excess of hydrogen above the stoichiometric equivalent, such as about 4 moles of hydrogen per mole of carbon oxide, preferably carbon monoxide. However, the ratio of reactants may be varied within fairly wide limits as recognized in the art.

For instance, as discussed previously, a coal or char gasifier producing a low ratio $H_2/CO$ syngas requires less investment than that to produce high $H_2/CO$ ratio syngas because of the large steam and oxygen requirements for high ratio gas. Because of these large and significant differences in investment and energy requirements in preparing steam and oxygen, the relative amounts of these reactants rquired in a char or coal gasification operation have an important bearing on the thermal efficiency of the process. That is, the highest efficiency occurs at the lowest steam to oxygen ratio that satisfies the stoichiometry for an $H_2/CO$ ratio gas of about 0.50 and the operating temperature constraints of the operation. It may be said that the generation of steam used in a gasifier is equivalent to using oxygen instead of air to combust coal and is therefore more expensive and less efficient.

Low ratio syngas ($H_2/CO = 1/1$ or less) is not detrimentally critical to this process, and utilization of a Fischer-Tropsch catalyst containing or provided with water gas shift characteristics in the slurried catalyst reactor system can be relied upon for effecting high conversions of $H_2$ and CO when processing both low and higher ratio syngas feed. The importance of the processing combination becomes even more interesting when it is recognized that a low cost syngas generation operation can be taken advantage of in contributing to the overall economics of the process by maximizing the recovery of heat from the exothermic reaction by steam generation and utilizing steam thus generated by the Fischer-Tropsch slurry operation for generating reactants for the syngas generation operation. That is, it is much less costly to generate a low $H_2/CO$ syngas, 1/1 or less, than it is to generate a higher ratio syngas. Furthermore, a low ratio syngas in the range of 0.4 to 0.7 can be adjusted by the water gas shift activity of a Fischer-Tropsch catalyst on a oncethrough basis to provide high yields of $C_3+$ hydrocarbons and oxygenates. The reaction mechanisms by which hydrocarbons are formed from syngas over different catalyst compositions have been studied and reported on by many researchers in the field.

If a low ratio synthesis gas (1/1 or less $H_2/CO$ ratio) is charged, it is essential that the carbon monoxide reducing catalyst used include water gas shift activity or characteristics so that steam formed in the Fischer- Tropsch operation by conversion of the low ratio synthesis gas will react with charged CO to form $H_2$. Examples of carbon monoxide reducing catalysts comprising shift activity are iron alone, or iron, cobalt, or ruthenium provided with an added shift catalyst component. Shift catalysts suitable for the purpose include those containing the elements Fe, Cr, Zn or Cu. It is also contemplated charging some steam with the synthesis gas of 0.7 $H_2/CO$ ratio or less.

It is important for temperature control in the slurried Fischer-Tropsch operation to maintain sufficient heat exchange fluid generally comprising a relatively high boiling portion of the synthesis hydrocarbon product in direct contact with the catalyst particles to substantially suspend the particles and maintain predetermined and desired temperature control and thus limit the buildup of coke on the catalyst particles. Thus, it is possible in the liquid phase Fischer-Tropsch operation to more closely restrict the temperature exotherm about any given particle within more narrow limits, to use more selective operating temperatures, and achieve results not obtainable in a fixed bed catalyst system. The level of liquid in the slurry reaction zone is maintained at desired level by the continuous withdrawal of vapors and liquid product. The recycle of a liquid product with catalyst particles concentrated therein to the reaction zone following temperature adjustment is pursued as required.

The liquid used for the suspension of the catalyst is preferably a hydrocarbon oil product of a boiling range which, under the conditions of temperature and pressure at which carbon monoxide hydrogenation proceeds, will not appreciably volatilize. Thus, for instance, it is preferred to use a hydrocarbon oil product fraction having a boiling point generally somewhat higher than the highest reaction temperature that is to be used in the conversion. Within the general scope of the invention, hydrocarbon product oil fractions boiling above 250° C. are normally satisfactory. Within the preferred embodiment of the invention, however, it is advantageous to use for the suspension of the catalyst an oil product as is obtained in the synthesis itself and having the requisite boiling range.

The catalyst useful in accordance with the invention may be any suitable catalyst conventionally employed for carbon monoxide hydrogenation in accordance with the Fischer-Tropsch type synthesis. Such catalysts contain, as known, metals of Group VIII of the Periodic Table, including iron, nickel, cobalt and ruthenium. To the extent that the catalysts employed for the synthesis in liquid medium in accordance with the invention are completely free from activators or consist of the Group VIII metals or their compounds only, it is desirable to add suitable activating substances conventionally known and used for synthesis of the Fischer-Tropsch type. Such activating substances include copper, thorium or magnesium or their compounds in quantities which do not exceed more than a few percent of the metal catalyst. Additional increases in activity can be achieved by adding alkali compounds to the catalyst, such as potassium or sodium.

In general, the reaction of this invention will be carried out at operating conditions well known for Fischer-Tropsch synthesis. Preferably, a low $H_2/CO$ ratio syngas, 0.5 to 1 and more, usually in the range of 0.5 to about 0.8, which is typically obtained by high efficiency gasification of coal as set forth in detail in U.S. Pat. No. 4,252,736 incorporated herein by reference, is converted in the slurry catalyst Fischer-Tropsch reactor at a temperature within the range of 400° F. up to about 600° F. and a pressure within the range of 50 to 1000 psig. The contact time of the syngas is chosen to provide high conversion per pass, at least 50%, preferably 70–95%. This value depends on the length of the reactor, the nature of the Fischer-Tropsch catalyst and its concentration in the slurry. The preferred catalyst is one comprised of 100 parts iron, 0.3 to 3.0 parts Cu and 0.1 to 1.5 parts $K_2CO_3$ by weight. Precipitated catalysts are preferred over supported catalysts. A space velocity between about 0.5 liter and 10 liters of syngas (STP) per gram iron per hour will provide the desired high conversion. Within these operating parameters, the temperature exotherm encountered by any given suspended catalyst particle in the liquid phase material is closely retained within the narrow limits, thereby contributing to a more satisfactory operation of the system for producing liquid products. The suspended catalyst particles retained in the liquid phase may be selected from within the range of about 1 to 50 microns, thereby providing a larger amount of surfaceactive sites than obtainable with larger size catalyst particles or extrudate used in fluid and fixed catalyst bed systems. The low temperature operation contemplated is particularly desirable for reducing the production of $C_1$ and $C_2$ hydrocarbons, for reducing carbon buildup on the catalyst and for improving selectivity operation for producing liquid hydrocarbon. Thus, not only is the liquid product selectively mantained high by the low temperature liquid slurry Fischer-Tropsch operation, but the use of a low cost gasifier which reduces gasification cost from 20 to 40% can be used to advantage with the slurry Fischer-Tropsch catalyst operation.

Optionally, a product of the Fischer-Tropsch synthesis operation separated from catalyst particles, other than that required for recycle to maintain the desired liquid phase, can be recovered for further processing as in U.S. Pat. No. 4,252,736 provided. This recovered material comprising liquid and gaseous components of the Fischer-Tropsch operation may be separated to recover oxygenates and $C_4^-$ gaseous components therefrom for treatment separately from $C_5^+$ gasoline and distillate boiling range hydrocarbons, or a total product mixture thereof without separation is passed in contact with a separate bed of the special zeolite catalyst and particularly represented by ZSM5 zeolite at a temperature in the range of 400° to 850° F. and a pressure in the range of 50–700 psig. The special zeolite catalyst is maintained under particularly desired activity and selectivity conditions to convert ethylene, $C_3^+$ or $C_5^+$ hydrocarbons with and without oxygenates, either separately or together, to premium hydrocarbon products including higher octane gasoline boiling range products and/or distillate fuels and lubes. The $C_4^-$ gaseous hydrocarbons are processed by one of alkylation or polymerization to produce high octane gasoline boiling material. Alternatively, the gaseous products can be recovered as SNG and LPG.

During normal operation a high molecular weight wax product will be produced. The amount of wax produced will vary depending upon reaction conditions. In any event, the wax product must be periodically withdrawn to prevent wax buildup in the slurry reactor and to prevent gellation of the reaction product. Gellation eventually leads to a shutdown of the reactor, and thus must be avoided. The wax product which is withdrawn from the reactor, however, contains catalyst fines entrained therein which need to be removed prior to upgrading the wax product. A portion of the catalyst fines, however, are smaller than 1 micron in size, such that ordinary filtration is ineffective for fines removal and filtration using filter aids is time prohibitive and will not permit catalyst recovery.

In accordance with the present invention, separation of iron catalyst fines from the wax product which has been removed from a slurry Fischer-Tropsch reactor is accomplished by high gradient magnetic separation. Briefly, such separation is accomplished by melting the wax product and passing the melted wax through a separator capable of generating a very high magnetic field gradient. In the simplest design, the high gradient magnetic separator comprises steel wool packed within a tube which is positioned between the poles of an electromagnet. The wax product containing the iron catalyst fines is passed through the tube and the steel wool, while the iron fines entrained in the wax are held by the magnetized steel wool. Removal of substantially all of the fines from the wax product has been achieved by high gradient magnetic separation as disclosed herein. Additional catalyst fines may be removed by filtration using a filter aid. Reference is made to the article by Hirschbein et al, discussed previously in regard to the specific theoretical mechanism which explains the manner in which the high gradient magnetic fields are developed. The separation system of the present invention is remarkably efficient in removing small catalyst particles which are entrained in the hydrocarbon products from the slurry Fischer-Tropsch reactor. It is believed that the formation of high gradient magnetic fields is the primary reason for the efficient separation observed.

The employment of high gradient magnetic separation in the context of removing iron Fischer-Tropsch catalyst fines from a wax product which is recovered from a slurry Fischer-Tropsch reactor as in the present invention can be best explained by referring to the accompanying drawing. In the FIGURE, reference numeral 10 refers to a slurry bubble-column Fischer-Tropsch reactor which contains a column of iron catalyst dispersed within a hydrocarbon carrier to form a slurry. The hydrocarbon carrier may include a portion of the hydrocarbon product produced upon the hydrogenation of carbon monoxide. The syngas is directed to reactor 10 via line 14 and is discharged into the reactor at the bottom thereof. Gaseous and lower molecular weight hydrocarbon liquids formed in slurry reactor 10 are withdrawn from the top and may optionally be directed to a second stage reactor for conversion in the presence of ZSM-5, as discussed in U.S. Pat. No. 4,252,736. Such product leaves reactor 10 via line 16. The high molecular weight wax product is withdrawn from slurry 12 via line 18. Entrained within the wax product will be a substantial amount of catalyst fines which must be removed prior to upgrading the wax. The removal of the catalyst fines from the wax product is achieved by a high gradient magnetic separation scheme as illustrated in the FIGURE. The FIGURE illustrates the use of two parallel high gradient magnetic separators, but it is to be understood that other separation schemes, such as a single separator or a plurality of separators in series, will produce the desired results. Specifically, in the separation scheme illustrated in the FIGURE, high gradient magnetic field separators 20 and 22 are placed in parallel arrangement in which wax product from line 18 is divided into equal portions and each portion is passed through one of separators 20 or 22 for the separation of the catalyst fines therefrom. Each individual high gradient magnetic separator comprises a means 24 to hold a filter element 26. Means 24 can comprise a hollow tube in its simplest construction. Filter element 26 can comprise steel wool, thin filaments, or thick filaments such as bars or the like which are capable of being magnetized in the presence of a magnetic field. The high magnetic field gradients are generated by the thin filaments or by small features such as ridges or other surface irregularities on the larger elements. Tube 24 is positioned such that filter element 26 is positioned between the poles of an electromagnet 28. Filter element 26 is magnetized by the magnetic field formed between the opposite poles of magnet 28. Catalyst separation from the wax and catalyst recycle are readily accomplished by turning electromagnet 28 on and off, as will be more fully explained below. Wax from line 18 is divided and passed to the respective high gradient magnetic separators 20 and 22 from feed line 30. The wax is generally heated for flow through tube 26. Upon the application of an electrical current to electromagnet 28, filter element 26 is magnetized. As the wax flows through tube 24 and past filter element 26 the entrained catalyst fines will be drawn to magnetized filter element 26 and trapped or held thereon while the purified wax flows out through confining means 24. The purified wax is tapped from discharge line 32 for further processing via line 34. When it is desirable to recycle the separated catalyst particles to slurry reactor 10, the electric current is switched off and the purified wax leaving each of the magnetic separators is flushed back through filter element 26, whereupon the mixture of wax and catalyst is returned to slurry reactor 10 via recycle lines 36 and 38. Preferably, a solvent is added to the purified wax via line 40 before the filter element is washed. The solvent can be a hydrocracked product from the purified wax. The solvent and wax which is sent back to the slurry will reduce the congelling point of the wax slurry and thereby lengthen the reaction on stream time.

Before upgrading the purified wax product, the product from the high gradient magnetic separator may be passed in contact with an acidic solid, such as alumina or an aluminosilicate zeolite, whereupon soluble potassium compounds in the wax are ion-exchanged and basic nitrogen compounds, if present, are absorbed. This subsequently purified wax product can then be directed to further processing, such as hydrogenation, hydrocracking, etc., as discussed previously.

The following examples illustrate the ability of high gradient magnetic separation to remove iron catalyst fines from the wax product obtained in a Fischer-Tropsch slurry reactor.

EXAMPLES

Separation of Catalyst Fines From Slurry Bubble Column Wax

| | Treatment | | | |
| --- | --- | --- | --- | --- |
| | Example 1 | | Example 2 | |
| PPM | None | HGMS | None | HGMS |
| Iron | 7600 | 35 | 15000 | 56 |
| Copper | 170 | 14 | 215 | 3 |
| Potassium | 8 | 15 | 510 | 21 |
| Nitrogen | 40 | 50 | — | — |
| Weight, % | | | | |
| Solids | 2 | 0.01 | 3 | 0.04 |

-continued

| | Treatment | | | |
|---|---|---|---|---|
| | Example 1 | | Example 2 | |
| PPM | None | HGMS | None | HGMS |
| Solids Removed | — | 99.5 | — | 98.6 |

It can clearly be seen that over 98% of the iron and solids are removed from the wax.

DESCRIPTION OF THE PREFERRED EMBODIMENT

In the preferred embodiment shown in the FIGURE of the drawings, it is desired to provide a continuous process whereby magnetic particles may be continuously separated from the high molecular weight wax product to produce a purified wax product substantially devoid of magnetic catalyst or other magnetic particles. This preferred embodiment may be fully understood with reference to the FIGURE of the drawings, in which the waxy product is withdrawn through line 18 by means of pump 58, which delivers the waxy product with entrained magnetic catalyst or other magnetic fines to feed line 30. Feed line 30 is provided with valves 44 and 48, which permit the aforementioned waxy product with entrained magnetic catalyst or fines to be fed to each of magnetic field separators 20 and 22 for separation of the magnetic catalyst and fines from the waxy product to form a purified wax product which is withdrawn through valves 50 and 54 into discharge line 32 for further processing via line 34. The magnetic catalyst and fines are temporarily retained in the filter elements of each of magnetic field separators 20 and 22, i.e., in filter 26.

In the most preferred embodiment of applicants' invention, there is a continuous withdrawal of waxy product with entrained magnetic catalyst or fines through line 18 by means of pump 58 fed continuously through at least one of high gradient magnetic field separators 20 and 22. This is not to state that the stream of waxy product with magnetic particles cannot be split at line 30 and fed to each of magnetic separators 20 and 22 by opening both valves 44 and 48, but that during backwash of one of magnetic separators to remove the entrained magnetic particles from the filter, the other magnetic separator will continuously process the withdrawn waxy product with entrained magnetic particles to separate the same into purified wax product substantially devoid of particles. This will be further understood again with reference to the following description of the FIGURE.

Waxy product with entrained magnetic catalyst or fines is continuously withdrawn through line 18 by means of pump 58 and is fed to feed line 30. However, only one of valve 44 and 48 will be open, with the other valve remaining closed. For example, with valve 44 open and valve 48 closed, the waxy product with entrained magnetic catalyst and fines is fed through high gradient magnetic separator 20 when valve 50 is open, permitting access of the purified wax product to discharge line 32 and line 34 for further processing. At this time valve 52 is normally closed. However, at the same time that purified wax product is exiting through lines 32 and 34, a portion thereof may be used to backflush the filter element in high gradient magnetic separator 22 by opening valves 54 and 56, while terminating the field in high gradient magnetic separator 22. The magnetic particles entrained in the filter element will be backwashed through valve 56 and line 36 by means of pump 60 for return via line 38 to the slurry 12 in reactor 10. The backwashing of the magnetic filter element by a purified wax product may be further facilitated by opening valve 46, allowing a portion of solvent to mix with the purified wax product for purposes of enhancing the cleaning of the filter element. This solvent is also returned to slurry 12, where it reduces the congealing point of the slurry 12 and thereby lengthens the reaction on-stream time. Of course, by backflushing the filter elements, the entrained magnetic catalyst particles removed from the filter elements by the cleaning process reenter slurry 12 in reactor 10, thereby maintaining a high percentage of catalyst-to-hydrocarbon ratio. Thus, the ratio of catalyst to slurry is maintained substantially constant.

Backflushing of filter element 26 of high gradient magnetic separator 20 is accomplished in a similar manner by closing valves 44 and 56 while opening valve 48 so as to permit the waxy product with entrained magnetic catalyst and fines to flow through high gradient magnetic separator 22. Valve 46 is then closed and valves 50, 52 and 54 opened so as to permit a backwashing and cleaning of filter element 26 by a portion of purified wax product exiting high gradient magnetic separator 22. Where appropriate, valve 42 may be opened to permit a portion of a solvent to be admixed with the purified wax product to assist and facilitate the cleaning of filter element 26. Of course, this backwashed material, including magnetic catalyst and fines, will pass through valve 52 by means of pump 60 to be fed back to slurry 12 through line 38 in a manner similar to that performed when high gradient magnetic separator 22 was backwashed. Although the foregoing process was described with reference to only two high gradient magnetic separators connected in parallel, as shown in the instant FIGURE, it is to be understood that more than two magnetic separators may be connected in parallel, provided that the connections permit the continuous withdrawal of waxy product containing magnetic catalyst and fines with simultaneous backwashing of at least one of the filter elements contained within said high gradient magnetic separators.

Although the present invention has been described with preferred embodiments, it is to be understood that modifications and variations may be resorted to, without departing from the spirit and scope of this invention, as those skilled in the art will readily understand.

What is claimed is:

1. In an improved process for converting synthesis gas comprising hydrogen and carbon monoxide to hydrocarbons by means of a slurry Fischer-Tropsch synthesis wherein a catalyst having activity for reducing carbon monoxide is dispersed in a liquid to form a slurry in a reaction zone and a wax product is produced by said synthesis in said reaction zone, said wax product having magnetic catalyst fines contained therein, the improvement comprising:

removing said wax product from said slurry and passing said removed wax product through high magnetic field gradients, said high magnetic field gradients being produced by a magnetic filter element placed between the poles of a magnet, said wax product being passed through said filter element, whereby said catalyst fines are held by said magnetic field gradients and separated from said wax product to yield a purified wax product and separated catalyst fines, turning off said magnetic field, and backwashing said filter element with a portion of said purified wax product to return said catalyst fines to said slurry in said reaction zone, whereby the ratio of catalyst-to-slurry is maintained substantially constant.

2. The improvement of claim 1, wherein said catalyst comprises iron.

3. The improvement of claim 2, wherein substantially all of said separated catalyst is returned to said slurry.

4. The improvement of claim 2, wherein said magnet is an electromagnet and said magnetic filter element is a nonmagnetic element which is magnetized upon the application of an electric current to said electromagnet.

5. The improvement of claim 4, wherein substantially all of said catalyst is returned to said slurry by terminating the application of said electric current and washing said filter element to remove said held catalyst.

6. The improvement of claim 5, wherein there is more than one of said filter element and each is washed by a portion of said purified wax product.

7. The improvement of claim 6, wherein a solvent is added to said purified wax product prior to washing each said filter element.

8. The improvement of claim 2, wherein said purified wax product is further upgraded in the presence of a catalyst.

9. The improvement of claim 2, wherein said catalyst further comprises a potassium promoter.

10. The improvement of claim 2, wherein said purified wax product is further treated with an acidic solid to remove potassium and nitrogen compounds from said purified wax.

11. The improvement of claim 2, wherein the ratio of $H_2/CO$ in said synthesis gas is not greater than 1.

12. In a processing combination comprising the steps of coal gasification to produce $H_2$ and $CO$, Fischer-Tropsch hydrocarbon synthesis from said $H_2$ and $CO$ and upgrading the product of Fischer-Tropsch synthesis to produce more desirable gaseous hydrocarbon products, gasoline and distillate material wherein said coal gasification is carried out in a gasifier characterized by:

(1) being capable of producing syngas with less than 30 lbs. of steam per MSCF of syngas, (2) producing a low ratio syngas with a $H_2/CO$ ratio of 0.4 to 1, and (3) a gasifier exit gas temperature of less than 2000° F., and said low ratio $H_2/CO$ syngas is fed to a Fischer-Tropsch Syngas conversion zone comprising a catalyst providing water gas shift and CO-reducing characteristics in a single or a combination of catalyst particles in direct contact with a suspending liquid medium providing temperature control of the exothermic syngas conversion reaction about the particle of catalyst, recovering heat from said Fischer-Tropsch syngas conversion zone in the form of medium pressure steam and utilizing said steam in said coal gasifier or its associated oxygen generation plant;

recovering a product of said Fischer-Tropsch syngas conversion comprising a hydrocarbon in a range of $C_1$–$C_{80}$ hydrocarbons and oxygenates, and converting at least a portion of the hydrocarbons and oxygenates recovered from said Fischer-Tropsch operation with a special crystalline zeolite catalyst of the ZSM-5 type to premium products comprising gaseous LPG products, gasoline and distillate material;

the improvement which comprises:

continuously removing a wax product stream in the range of $C_{10}$–$C_{80}$, which has accumulated in the conversion zone, said wax product having magnetic catalyst fines contained therein and continuously passing said removed wax product stream through at least one of two high magnetic field gradients, each of said high magnetic field gradients being produced by a magnetic filter element placed between the poles of a magnet, said filter elements being arranged in parallel, said wax product stream continuously being passed alternately through at least one of said parallel filter elements, while the other is being backwashed with purified wax product.

13. The improvement of claim 12, wherein said catalyst comprises iron.

14. The improvement of claim 13, wherein substantially all of said separated catalyst is returned to said conversion zone.

15. The improvement of claim 13, wherein said magnet is an electromagnet and said magnetic filter element is a nonmagnetic element which is magnetized upon the application of an electric current to said electromagnet.

16. The improvement of claim 15, wherein said catalyst is returned to said conversion zone by terminating the application of said electric current and washing said filter element to remove said held catalyst.

17. The improvement of claim 16, wherein each of said filter elements is alternately washed by a portion of said purified wax product.

18. The improvement of claim 17, wherein a solvent is added to said purified wax product prior to washing each said filter elements.

19. The improvement of claim 13, wherein said purified wax product is further upgraded in the presence of a catalyst.

20. The improvement of claim 13, wherein said catalyst further comprises a potassium promoter.

21. The improvement of claim 13, wherein said catalyst further comprises a Cu promoter.

22. The improvement of claim 13, wherein said purified wax product is further treated with an acidic solid to remove potassium and nitrogen compounds from said purified wax.

23. The process of claim 12, wherein said syngas conversion operation is maintained at a temperature in the range of 400° to 600° F., a pressure in the range of 50 to 1000 psig, and a space velocity to achieve at least 50% conversion, and said portion of the product of said Fischer-Tropsch operation in contact with a ZSM-5 type zeolite conversion catalyst maintained at a temperature in the range of 400° to 850° F. and a pressure in the range of 50 to 700 psig and recovering as product of the combination operation a high octane gasoline product and a low pour diesel oil.

24. The process of claim 12, wherein the thermal efficiency of the coal gasification operation is at least 70%.

25. The process of claim 12, wherein a part of the product of syngas conversion is used to suspend the CO-reducing catalyst and the crystalline zeolite catalyst is HZSM-5 type zeolite.

26. The process of claim 12, wherein the CO-reducing component comprises water gas shift activity.

27. The process of claim 12, wherein the CO-reducing component is admixed with a water gas shift catalyst component.

28. The process of claim 12, wherein said portion of the hydrocarbons and oxygenates of the Fischer-Tropsch operation are passed together as a mixture over a bed of ZSM-5 type zeolite catalyst for conversion to premium products.

29. The process of claim 12, wherein the liquid hydrocarbon product of Fischer-Tropsch synthesis is separated to recover gasoline boiling range material from distillate material and each is thereafter separately processed over ZSM-5 type zeolite catalyst to produce high octane gasoline and diesel fuel.

30. The process of claim 12, wherein $C_4^-$ gaseous hydrocarbons are processed by one of alkylation or polymerization to produce higher octane gasoline boiling material.

31. The process of claim 12, wherein the gaseous products of Fischer-Tropsch synthesis and ZSM-5 type catalyst conversion are recovered as SNG and LPG.

32. The process of claim 12, wherein water or steam is added to the Fischer-Tropsch conversion zone.

33. The process of claim 12, wherein the light gaseous products of the Fischer-Tropsch operation comprising $H_2$, CO and $C_2^-$ hydrocarbons are cryogenically separated, the separated $H_2$ and CO gases are recycled to the Fischer-Tropsch operation and a portion of the $C_2^-$ hydrocarbons is used as fuel gas in the processing combinations.

* * * * *